United States Patent [19]

Sabin

[11] Patent Number: 4,847,082

[45] Date of Patent: Jul. 11, 1989

[54] METHOD OF TREATMENT OF ALZHEIMER'S DISEASE USING PHYTIC ACID

[75] Inventor: Robert Sabin, Goosedown Estate, Box 332 Horseshoe Rd., Mill Neck, Long Island City, N.Y. 11765

[73] Assignee: Robert Sabin, Long Island, N.Y.

[21] Appl. No.: 177,690

[22] Filed: Apr. 5, 1988

Related U.S. Application Data

[62] Division of Ser. No. 5,995, Jan. 21, 1987, Pat. No. 4,758,430.

[51] Int. Cl.$^4$ .............................................. A61K 37/48

[52] U.S. Cl. ................................. 424/103; 424/94.1; 514/102

[58] Field of Search .................................. 424/94.1, 94

Primary Examiner—Stanley J. Friedman
Attorney, Agent, or Firm—Flehr, Hohbach, Test, Albritton & Herbert

[57] ABSTRACT

A method is provided for treating Alzheimer's Disease by administering to a subject an effective symptom-alleviating amount of a compound selected from the group consisting of phytic acid, phytate salt, an isomer or hydrolysate of phytic acid or phytate salt, or a mixture of any combination thereof. The preferred method of administration is by oral dosages of about ½ to 3 grams/kilogram bodyweight per day.

7 Claims, No Drawings

METHOD OF TREATMENT OF ALZHEIMER'S DISEASE USING PHYTIC ACID

This is a division of application Ser. No. 005,995 filed Jan. 21, 1987, now U.S. Pat. No. 4,758,430.

The present invention is directed to a method for treating Alzheimer's Disease by use of phytic acid, its salts or hydrolysates.

BACKGROUND OF THE INVENTION

Phytic acid, generally accepted as having the structure myo-inositol-hexakis (dihydrogen phosphate), is a major component of plant seeds, constituting 1–3% by weight of many cereals and oil seeds. Most wheat brans contain between 4 and 5% phytic acid. Phytic acid may be prepared in pure form from various plant sources, such as wheat, corn, soybeans, sesame seeds, peanuts, lima beans, barley, oats, wild rice and sunflower seeds. It can be extracted with dilute hydrochloric acid at room temperature, precipitated with various reagents including ferric chloride, bicarbonates, potassium hydroxide, sodium hydroxide, ammonium hydroxide, calcium hydroxide, magnesium hydroxide or alcohol. It is then further purified by conventional chemical techniques.

When one or more of the acidic protons of the phosphate groups in phytic acid are replaced by a counterion, the compound is usually referred to as a phytate salt. The special name phytin is used for the calcium-magnesium salt of phytate derived from plant seeds (a product of Ciba-Geigy). The present invention includes the use not only of phytic acid and phytate salts, but also various isomeric forms of phytic acid and phytate salts. While the Anderson structure for myo-inositol hexakis dihydrogen phosphate is the accepted structure for phytic acid, the present invention covers other isomers which have been previously described in the literature. These isomers include the cis, epi, allo, muco, neo, D-chiro, L-chiro, and scyllo configurations.

Also, while phytic acid contains six phosphate groups, when introduced into the digestive tract of an animal, one or more of the phosphate groups may be hydrolyzed by the action of the digestive acids and enzymes. Therefore, the present invention includes the use of hydrolysates of phytic acid and phytate salts wherein one or more of the phosphate groups have been removed.

The main uses of phytic acid include use as a food additive for preservation of foods. Studies on the use of phytic acid as a food additive show that ingestion of large doses of phytic acid elicits no physiological discomfort or symptoms of any toxicological action in humans. See Starkenstein, *Biochem. Z.* 30: 56 (1911). Phytic acid and its metabolites are thus not believed to be toxic or highly reactive.

Medical applications of phytic acid include use as an imaging agent for organ scintography, an X-ray enhancement contrasting agent and use to reduce gastric secretion for treatment of gastritis, gastroduodenitis, gastric duodenal ulcers and diarrhea. It has been suggested as an antidote for toxic metal absorption, for therapeutic use in the prevention and dilution of calcium deposits associated with various diseases and for reducing calcium concentration in urine (thus checking the formation of renal calculi). Other uses include as a preventive agent against severe poisoning with pressurized oxygen and preventing thirst during exercise. It has been used as a counterion in salts with various orally administered antibiotics to improve taste.

Phytic acid has also been suggested to reduce the incidence of dental caries, and has been utilized in dentifrices, mouth rinses, dental cements, cleaning agents for dentures and for removing nicotine tar from teeth.

Industrial uses of phytic acid include use as a corrosion inhibitor on metals, a rust remover and an additive to lubricating greases. Other miscellaneous uses of phytic acid include oral administration to treat acne, to improve skin color, blood circulation and fingernail growth; and as an additive in cosmetics for anti-dandruff hair lotions and skin care lotions. One potential agricultural use of phytic acid is to inhibit aflatoxin production by *Aspergillus parasiticus*. It is also useful as an additive to a fermentation medium containing *Micromonospora sagamiensis* in the fermentative production of antibiotics. Similarly, phytic acid may be used as a growth-promoting factor in the fermentation medium for the cultivation of yeast for feed.

For further discussions of industrial applications of phytic acid, see Graf, *JAOCS* 60, 1861–1867 (1983).

Although the above description indicates the broad scope of potential uses of phytic acid, there is not believed to be any suggestion in the prior art that phytic acid is useful for the treatment of Alzheimer's Disease.

Accordingly, it is an object of the present invention to provide a method for treatment of Alzheimer's Disease by use of phytic acid, phytate salts, and isomers or hydrolysates thereof.

This and other objects will be made apparent by the following description of the preferred embodiments and appended claims.

SUMMARY OF THE INVENTION

The present invention provides a method of treating Alzheimer's Disease, comprising the step of administering to a subject a symptom-alleviating dose of a compound, selected from the group consisting of phytic acid, a phytate salt, an isomer or hydrolysate of phytic acid or a phytate salt, or a mixture of any combination thereof. The preferred method of administration is by the oral route.

DESCRIPTION OF THE PREFERRED EMBODIMENTS

The method according to the present invention comprises treating a subject, afflicted with Alzheimer's Disease, with a composition in which the active ingredient is phytic acid, a phytate salt, or an isomer or hydrolysate of phytic acid or phytate salt. By the term isomer as used herein, it is intended to include the various conformations of phytic acid, as described hereinabove, and the corresponding conformations of phytate salts. The term salts is broadly intended to cover any of the various salts formed by the replacement of any or all of the available acidic protons of the phosphate groups with a counterion. The counterion may be any pharmaceutically acceptable counterion such as sodium, magnesium, potassium, zinc, ferric, ferrous, and the like, including organic counterions such as quaternary ammonium ions and ions of organic bases.

The present invention also includes the hydrolysates of phytic acid and phytate salts wherein one or more of the phosphate groups have been removed. Once administered into the digestive tract, bloodstream, the phytic acid or phytate salt may be hydrolyzed by digestive, blood or cellular enzymes, thereby removing one or more of the phosphate groups on the cyclohexane ring. However, it is contemplated to be within the scope of the invention that these hydrolysates of phytic acid and phytate salts may also be administered directly to the subject and therefore are within the scope of the present invention.

The hydrolysates of phytic acid and phytate salts may be prepared by partial acid or basic hydrolysis or by hydrolysis using enzymes prior to preparation of dosage forms for administration. Preferably, the hydrolysates will be made in vivo by coadministering with phytic acid or phytate salt an enzyme which hydrolyzes phosphate groups, such as 3-phytase, 6-phytase or acid phosphatase.

The phytic acid or phytate salt may be absorbed into or adsorbed onto a solid carrier to facilitate pharmaceutical administration. For example, phytic acid may be formulated into a starch powder by spray drying or vacuum drying an aqueous mixture of phytic acid and dextrin.

The preferred compositions for administration, particularly in oral dosage form, are the mono-, di-potassium phytate salts and mixtures thereof which may be prepared from commercially and readily available sodium phytate by initially removing the sodium using ion exchange chromatography on a suitable resin, such as Dowex beads. The free phytic acid may then be treated with potassium hydroxide to convert to the mono- and di-potassium phytate salt.

The preferred method of administration of the compositions according to the present invention is through oral administration in liquid or tablet form. As described hereinabove, the compositions may be administered as pharmaceutically acceptable salts such as salts with alkali metal cations (sodium, potassium, lithium), ammonium salts and salts with organic bases such as piperidine, triethanolamine, diethylaminoethylamine salts, and the like.

In addition to the active ingredients, the composition may also contain an effective proportion, usually from 0.001 to 0.1% weight by volume, of a pharmaceutically acceptable preservative or sterilizing agent such as cetyl pyridinium chloride, tetradecyltrimethyl ammonium bromide (commercially known as Centramide), benzyl dimethyl [2-(2-)p-(1,1,3,3-tetramethyl butyl))phenoxy)ethoxy]ammonium chloride (known commercially as Benzethonium Chloride) and myristyl-gamma-picolinium chloride.

The pharmaceutical composition may also contain conentional excipients, e.g., sodium chloride, dextrose, mannitol, and buffers such as sodium dihydrogen ortho phosphate, disodium hydrogen phosphate, sodium citrate/citric acid, and boric acid/sodium borate. The proportion and concentration of excipients and buffers may be varied within fairly wide ranges, providing the resulting solution is stable and nonirritating when administered. The preferred method of administration is by oral administration as a solid compound. The composition may be prepared in the conventional manner as tablets, pills or powders, using conventional carriers.

The dosage to be administered will vary with the severity of the diseased condition. However, in general, particularly for oral administration, oral administration of from ½ to 3 grams of phytic acid (or equivalent phytate salt, isomer or hydrolysate) per kilogram of body weight in the diet per day will usually be effective. Frequency of dosage administration may, of course, be varied as needed and as discretionarily required by the attending physician.

For oral administration, in a preferred embodiment, the active ingredient of the composition will also contain an enzyme such as 3-phytase (EC 3.1.38), 6-phytase (EC 3.1.3.26) or acid phosphatase which, when exposed to the digestive tract, will assist in hydrolyzing one or more of the phosphate groups from the active ingredient. Since phytic acid or phytate salts are not naturally present in animals, the digestive enzymes in animals are believed to be insufficient to completely hydrolyze the phosphate groups. Therefore, to enhance the hydrolysis of the phosphate groups in an animal or man, it is preferred that the active ingredient be administered with one or more of the aforementioned enzymes, with the preferred enzyme being 3-phytase (EC 3.1.38).

I claim:

1. A method of treating Alzheimer's Disease in a subject comprising orally administering to said subject an effective symptom-alleviating amount of a compound selected form the group consisting of phytic acid, a phytate salt, an isomer or hydrolysate of phytic acid a or a phytate salt, or a mixture of any combination thereof.

2. A method according to claim 1 wherein said phytate salt comprises a potassium salt.

3. A method according to claim 2 wherein said phytate salt is selected form the group consisting of mono-, di-potassium phytate and mixtures thereof.

4. A method according claim 1 wherein said phytic acid is absorbed into a pharmaceutically acceptable carrier.

5. A method according to claim 1 wherein said isomers of phytic acid or phytate salt comprise the hexakisphosphate myo-inositol, scyllo-inositol, D-chiro-inositol, L-chiro-inositol, neo-inositol and muco-inositol conformations.

6. A method according to claim 5 wherein said isomer of phytic acid or phytate salt is the hexakisphosphate myo-inositol conformation.

7. A method according to claim 1 wherein said hydrolysate of phytic acid or phytate salt comprises the pentakisphosphate, tetrakisphosphate, triphosphate, diphosphate, monophosphate or completely dephosphorylated hydrolysate.

* * * * *